United States Patent
Grover et al.

(10) Patent No.: US 11,045,268 B2
(45) Date of Patent: Jun. 29, 2021

(54) INSTRUMENT DRIVE UNIT INCLUDING LEAD SCREW RAILS

(71) Applicant: Covidien LP, Mansfield, MA (US)

(72) Inventors: Simon R. Grover, Cambridge (GB); Charles F. Kilby, Cambridgeshire (GB); Daniel L. Fuller, Haverhill (GB); Alistair Ward, Swavesey (GB)

(73) Assignee: Covidien LP, Mansfield, MA (US)

(*) Notice: Subject to any disclaimer, the term of this patent is extended or adjusted under 35 U.S.C. 154(b) by 110 days.

(21) Appl. No.: 16/570,499

(22) Filed: Sep. 13, 2019

(65) Prior Publication Data
US 2020/0000534 A1    Jan. 2, 2020

Related U.S. Application Data

(63) Continuation of application No. 15/554,003, filed as application No. PCT/US2016/014213 on Jan. 21, 2016, now Pat. No. 10,420,618.
(Continued)

(51) Int. Cl.
*A61B 34/35* (2016.01)
*A61B 34/00* (2016.01)
(Continued)

(52) U.S. Cl.
CPC ............ *A61B 34/35* (2016.02); *A61B 34/30* (2016.02); *A61B 34/71* (2016.02); *A61B 46/10* (2016.02);
(Continued)

(58) Field of Classification Search
CPC ......... A61B 34/35; A61B 34/30; A61B 34/71; A61B 46/10; A61B 2034/302;
(Continued)

(56) References Cited

U.S. PATENT DOCUMENTS 7,886,743 B2   2/2011  Cooper et al.
8,337,515 B2   12/2012 Viola et al.
(Continued)

FOREIGN PATENT DOCUMENTS

EP       0705571 A1    4/1996
KR    20150018600 A    2/2015
(Continued)

OTHER PUBLICATIONS

Extended European Search Report issued in European Application No. EP 16756011.9 dated Oct. 2, 2018.
(Continued)

*Primary Examiner* — Erin M Piateski
(74) *Attorney, Agent, or Firm* — Carter DeLuca & Farrell LLP

(57) ABSTRACT

A surgical system for selective connection to a robotic arm includes an instrument drive unit and a surgical instrument detachably coupled to the instrument drive unit. The instrument drive unit includes first and second actuators and a first translatable member operatively coupled with the first actuator. The surgical instrument includes an adapter portion, an elongate member extending distally from the adapter portion, and an end effector mounted on a distal end of the elongate member. The adapter portion has a first rotatable member operatively associated with the first translatable member. The first rotatable member is rotatable in response to translation of the first translatable member. The end effector is operatively coupled with the first rotatable member, wherein rotation of the first rotatable member effects a first function of the end effector.

20 Claims, 6 Drawing Sheets

Related U.S. Application Data

(60) Provisional application No. 62/121,255, filed on Feb. 26, 2015.

(51) Int. Cl.
*A61B 46/10* (2016.01)
*A61B 34/30* (2016.01)
*A61B 17/00* (2006.01)
*A61B 17/072* (2006.01)

(52) U.S. Cl.
CPC ....... *A61B 17/00234* (2013.01); *A61B 17/072* (2013.01); *A61B 34/74* (2016.02); *A61B 2017/00199* (2013.01); *A61B 2017/00398* (2013.01); *A61B 2017/00477* (2013.01); *A61B 2017/00685* (2013.01); *A61B 2017/07278* (2013.01); *A61B 2034/302* (2016.02)

(58) Field of Classification Search
CPC .... A61B 2034/305; A61B 2018/00172; A61B 2018/00184; A61B 2018/00196; A61B 2018/00202; A61B 2018/00208; A61B 34/74; A61B 17/00234; A61B 17/072; A61B 2017/00199; A61B 2017/00398; A61B 2017/00477; A61B 2017/00685; A61B 2017/07278
USPC .......................................................... 606/1
See application file for complete search history.

(56) References Cited

U.S. PATENT DOCUMENTS

| 8,828,023 | B2 | 9/2014 | Neff et al. |
| 10,420,618 | B2 | 9/2019 | Grover et al. |
| 2006/0084945 | A1 | 4/2006 | Moll et al. |
| 2008/0308603 | A1* | 12/2008 | Shelton ............ A61B 17/07207 227/175.1 |
| 2009/0110533 | A1 | 4/2009 | Jinno |
| 2009/0248039 | A1 | 10/2009 | Cooper et al. |
| 2010/0175701 | A1 | 7/2010 | Reis et al. |
| 2010/0198253 | A1 | 8/2010 | Jinno |
| 2010/0204646 | A1 | 8/2010 | Plicchi et al. |
| 2011/0277775 | A1 | 11/2011 | Holop et al. |
| 2012/0116416 | A1 | 5/2012 | Neff et al. |
| 2013/0325034 | A1 | 12/2013 | Schena et al. |
| 2014/0005653 | A1 | 1/2014 | Shelton, IV et al. |
| 2014/0303434 | A1 | 10/2014 | Farritor et al. |
| 2015/0297199 | A1 | 10/2015 | Nicholas et al. |

FOREIGN PATENT DOCUMENTS

| WO | 2011060318 A1 | 5/2011 | |
| WO | 2011108840 A2 | 9/2011 | |
| WO | WO-2011108840 A2 * | 9/2011 | ............. A61B 34/70 |
| WO | 2013159932 A1 | 10/2013 | |
| WO | 2014005689 A2 | 1/2014 | |
| WO | 2014163787 A1 | 10/2014 | |
| WO | 2015012023 A1 | 1/2015 | |
| WO | 2015088647 A1 | 6/2015 | |

OTHER PUBLICATIONS

International Search Report for (PCT/US2016/014213) date of completion is May 13, 2016 (5 pages).

Chinese Office Action issued in CN Patent Application No. 201680011636.3, dated Sep. 4, 2019.

Second Chinese Office Action issued in CN Patent Application No. 201680011636.3, dated Jul. 9, 2020.

* cited by examiner

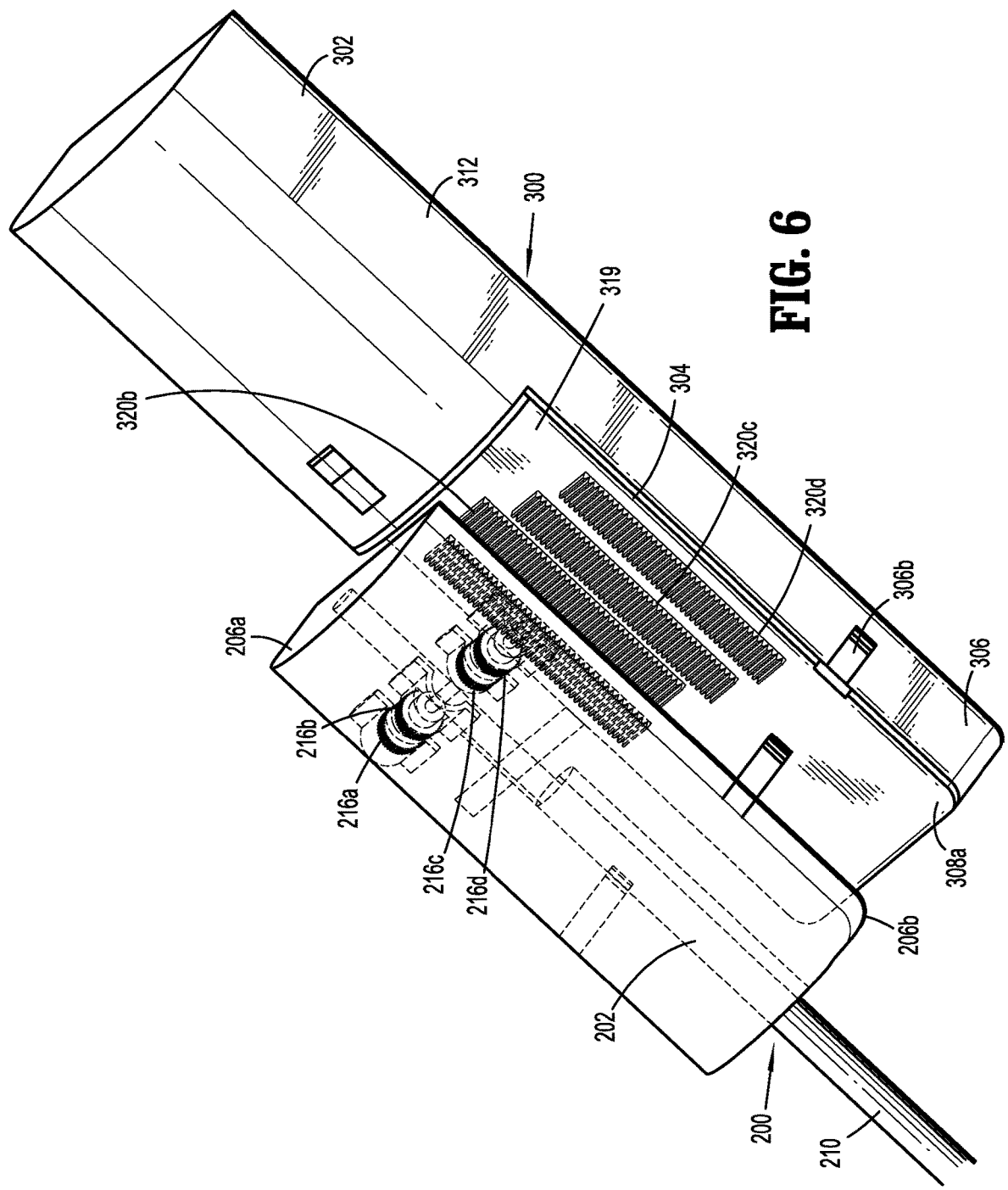

INSTRUMENT DRIVE UNIT INCLUDING LEAD SCREW RAILS

CROSS-REFERENCE TO RELATED APPLICATIONS

This application a continuation of U.S. patent application Ser. No. 15/554,003, filed on Aug. 27, 2017, now U.S. Pat. No. 10,420,618, issued on Sep. 24, 2019, which is a U.S. National Stage Application filed under 35 U.S.C. § 371(a) of International Patent Application Serial No. PCT/US2016/014213, filed Jan. 21, 2016, which claims the benefit of and priority to U.S. Provisional Patent Application Ser. No. 62/121,255, filed Feb. 26, 2015, the entire disclosure of each of which are incorporated by reference herein.

BACKGROUND

Robotic surgical systems used in minimally invasive medical procedures include a console or cart supporting a robot arm and a surgical instrument having an end effector that may include, for example, forceps, a stapler, or a grasping tool. The robot arm provides mechanical power to the surgical instrument for its operation and movement. Each robot arm may include an instrument drive unit that is operatively connected to the surgical instrument.

Prior to or during use of the robotic system, surgical instruments are selected and connected to the instrument drive units of each robot arm. For proper installation to be completed, certain connecting features of the surgical instrument must be matingly engaged to corresponding connecting features of the instrument drive unit. Once these features are matingly engaged, the instrument drive unit can drive the actuation of the surgical instrument. However, connection and removal of surgical instruments to instrument drive units can be difficult.

Accordingly, new robotic devices, systems, and methods that are reliable, precise, and that enable easy and efficient attachment and removal of surgical instruments would be desirable.

SUMMARY

The present disclosure describes robotic devices, systems, and methods that demonstrate a practical approach to meeting the performance requirements and overcoming the usability challenges associated with instrument attachment and removal. In general, the present disclosure describes robotic surgical systems that include an instrument drive unit and a surgical instrument support coupled to the instrument drive unit. The surgical instrument includes an end effector controllable to perform surgery in response to telemanipulation of actuators in the instrument drive unit.

In accordance with an embodiment of the present disclosure, there is provided a surgical system for selective connection to a robotic arm. The surgical system includes an instrument drive unit and a surgical instrument detachably coupled to the instrument drive unit. The instrument drive unit includes a first actuator and a first translatable member operatively coupled with the first actuator. The surgical instrument includes an adapter portion, an elongate member extending distally from the adapter portion, and an end effector mounted on a distal end of the elongate member. The adapter portion has a first rotatable member operatively associated with the first translatable member. The first rotatable member is rotatable in response to translation of the first translatable member. The end effector is operatively coupled with the first rotatable member, wherein rotation of the first rotatable member effects a first function of the end effector.

In an embodiment, actuation of the first actuator may cause translation of the first translatable member, which in turn, causes rotation of the first rotatable member of the adapter portion of the surgical instrument.

In another embodiment, the surgical instrument may further include a first cable having a first end coupled to the first rotatable member and a second end operatively associated with the end effector. In addition, the first rotatable member may include a reel portion configured to wind the first cable thereabout upon rotation of the first rotatable member. Furthermore, the first rotatable member may include a gear portion having teeth configured to mesh with teeth of the first translatable member of the instrument drive.

In yet another embodiment, the instrument drive unit may further include a second actuator operatively associated with the elongate member of the surgical instrument such that actuation of the second actuator causes rotation of the elongate member, which in turn, causes rotation of the end effector. In an embodiment, the second actuator may be slidably disposed such that the second actuator may be transitionable between a retracted position in which the second actuator is operatively disengaged from the elongate member and an extended position in which the second actuator is operatively engaged with the elongate member.

In still yet another embodiment, the first and second actuators of the instrument drive unit may be controlled by telemanipulation.

In still yet another embodiment, the instrument drive unit may further include a third actuator and a second translatable member operatively coupled to the third actuator. In addition, the adapter portion of the surgical instrument may include a second rotatable member operatively associated with the second translatable member. The second rotatable member may be rotatable in response to actuation of the third actuator. The first and second rotatable members may be independently rotatable.

The surgical instrument may further include a second cable having a first end coupled to the second rotatable member and a second end operatively associated with the end effector, wherein rotation of the first and second rotatable members effects the first function of the end effector. In an embodiment, the first and second rotatable members may rotate about a common axis.

In another embodiment, the surgical system may further include a drape interposed between the instrument drive unit and the surgical instrument to provide a sterile barrier.

In yet another embodiment, the teeth of the gear portion of the first rotatable member may engage the teeth of the first translatable member of the instrument drive through a sterile barrier.

In accordance with another aspect of the present disclosure, there is provided a robotic surgical assembly. The robotic surgical assembly includes a robotic arm, an instrument drive unit secured to the robotic arm, and a surgical instrument detachably coupled to the instrument drive unit. The instrument drive unit includes a plurality of actuators and a plurality of translatable members operatively coupled with respective one of the plurality of actuators. The surgical instrument includes an adapter portion and an elongate member. The adapter portion has a plurality of rotatable members operatively associated with the plurality of translatable members. Each rotatable member of the plurality of rotatable members is rotatable in response to actuation of the respective one of the plurality of actuators. The elongate member extends distally from the adapter portion, wherein rotation of one of the plurality of rotatable members causes a first function of an end effector.

BRIEF DESCRIPTION OF THE DRAWINGS

The accompanying drawings, which are incorporated in and constitute a part of this specification, illustrate embodiments of the disclosure and, together with a general description of the disclosure given above, and the detailed description of the embodiment(s) given below, serve to explain the principles of the disclosure, wherein:

FIG. 6 is a perspective view of the surgical assembly of FIG. 2 with the surgical instrument detached from the instrument drive unit;

DETAILED DESCRIPTION

Figure 1:
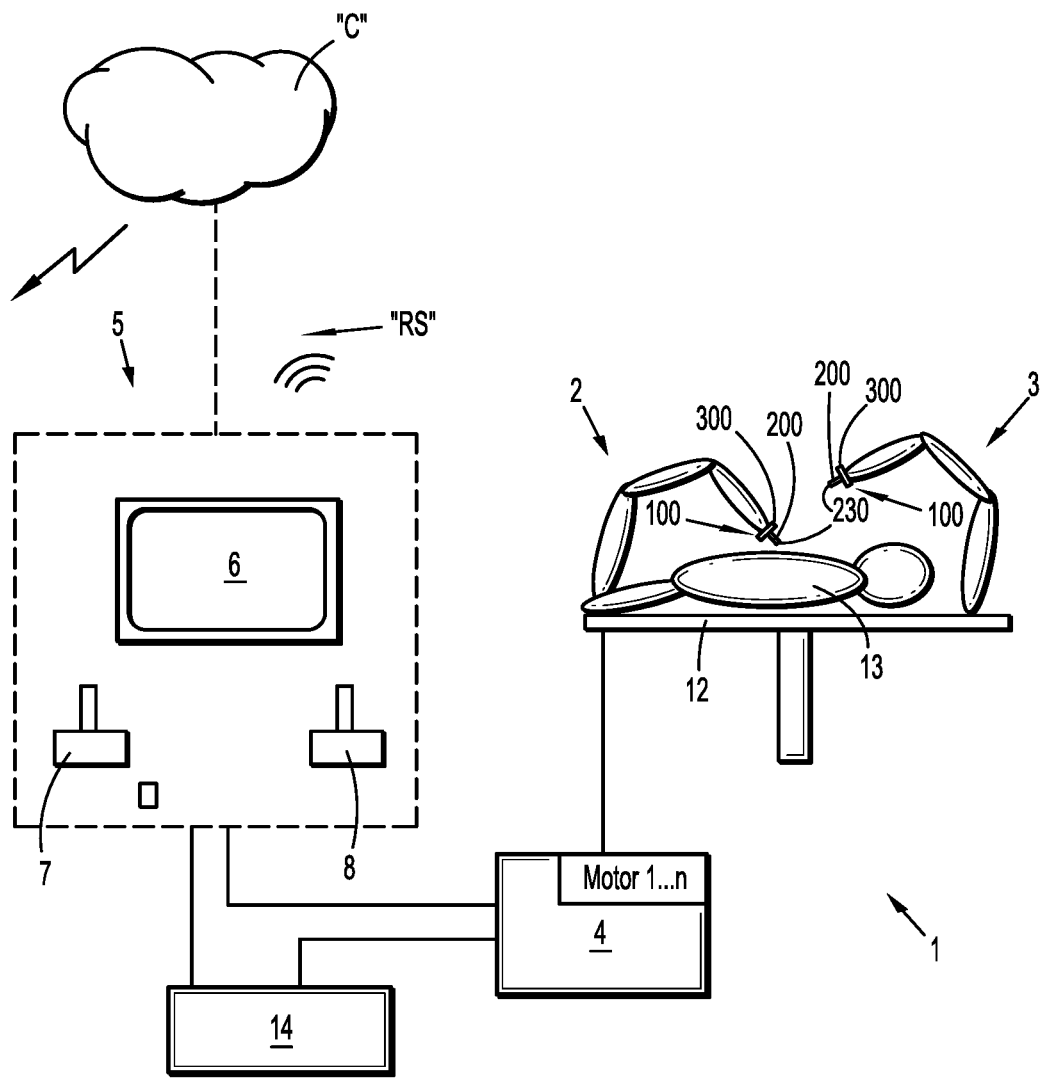
FIG. 1 is a schematic illustration of a robotic surgical system in accordance with the present disclosure.

Embodiments of the present disclosure are described in detail with reference to the drawings, in which like reference numerals designate identical or corresponding elements in each of the several views. As used herein, the term "distal" refers to that portion of a device that is farther from the user, while the term "proximal" refers to that portion of a device that is closer to the user.

With reference to FIG. 1, there is provided a robotic surgical system 1 including a plurality of robotic arms 2, 3; a control device 4; and an operating console 5 coupled with control device 4. Operating console 5 includes a display device 6 and manual input devices 7, 8, by means of which a person (not shown), for example a surgeon, is able to telemanipulate robotic arms 2, 3.

Each of the plurality of robotic arms 2, 3 includes a plurality of members, which are connected through joints. Robotic surgical system 1 also includes a surgical assembly 100 connected to a distal end of each of robotic arms 2, 3. Surgical assembly 100 includes an instrument drive unit 300 and a surgical instrument 200 detachably coupled to instrument drive unit 300. Surgical instrument 200 includes an end effector 230.

Robotic arms 2, 3 may be driven by electric drives (not shown) that are connected to control device 4. Control device 4 (e.g., a computer) is set up to activate the drives, in particular by means of a computer program, in such a way that robotic arms 2, 3, their surgical assemblies 100 execute a desired movement according to a movement defined by means of manual input devices 7, 8. Control device 4 may also be set up in such a way that it regulates movement of robotic arms 2, 3 and/or of the drives.

With continued reference to FIG. 1, robotic surgical system 1 is configured for use on a patient 13 lying on a patient table 12 to be treated in a minimally invasive manner by means of end effector 230. Robotic surgical system 1 may include more than two robotic arms 2, 3. The additional robotic arms may also be connected to control device 4 and may be telemanipulatable by means of operating console 5. One or more additional surgical assemblies 100 and/or surgical instruments 200 may also be attached to the additional robotic arm.

Control device 4 may control a plurality of motors (Motor 1 . . . n) with each motor configured to drive a pushing or a pulling of one or more cables such as cables 400a-d (FIG. 5) coupled to end effector 230 of surgical instrument 200. While cables are shown and described, it is also contemplated that cables can be replaced with rods or the like. In use, as these cables 400a-d are pushed and/or pulled, cables 400a-d effect operation and/or movement of end effector 230 of surgical instrument 200. It is contemplated that control device 4 coordinates the activation of the various motors (Motor 1 . . . n) to coordinate a pushing or a pulling motion of one or more cables 400a-d in order to coordinate an operation and/or movement of one or more end effectors 230. In embodiments, each motor can be configured to actuate a drive rod or a lever arm to effect operation and/or movement of end effectors 230 in addition to, or instead of, one or more cables 400a-d.

Control device 4 can include any suitable logic control circuit adapted to perform calculations and/or operate according to a set of instructions. Control device 4 can be configured to communicate with a remote system "RS," either via a wireless (e.g., Wi-Fi™, Bluetooth®, LTE™, etc.) and/or wired connection. Remote system "RS" can include data, instructions and/or information related to the various components, algorithms, and/or operations of robotic surgical system 1. Remote system "RS" can include any suitable electronic service, database, platform, cloud "C" (see FIG. 1), or the like. Control device 4 may include a central processing unit operably connected to memory. The memory may include transitory type memory (e.g., RAM) and/or non-transitory type memory (e.g., flash media, disk media, etc.). In some embodiments, the memory is part of, and/or operably coupled to, remote system "RS."

Control device 4 can include a plurality of inputs and outputs for interfacing with the components of robotic surgical system 1, such as through a driver circuit. Control device 4 can be configured to receive input signals and/or generate output signals to control one or more of the various components (e.g., one or more motors) of robotic surgical system 1. The output signals can include, and/or can be based upon, algorithmic instructions which may be pre-programmed and/or input by a user. Control device 4 can be configured to accept a plurality of user inputs from a user interface (e.g., switches, buttons, touch screen, etc. of operating console 5) which may be coupled to remote system "RS."

A database 14 can be directly and/or indirectly coupled to control device 4. Database 14 can be configured to store pre-operative data from living being(s) and/or anatomical atlas(es). Database 14 can include memory which can be part of, and/or or operatively coupled to, remote system "RS." Reference may be made to U.S. Patent Publication No. 2012/0116416, filed on Nov. 3, 2011, entitled "Medical Workstation," (now U.S. Pat. No. 8,828,023), the entire content of which is incorporated herein by reference, for a detailed discussion of the construction and operation of robotic surgical system 1.

Figure 2:
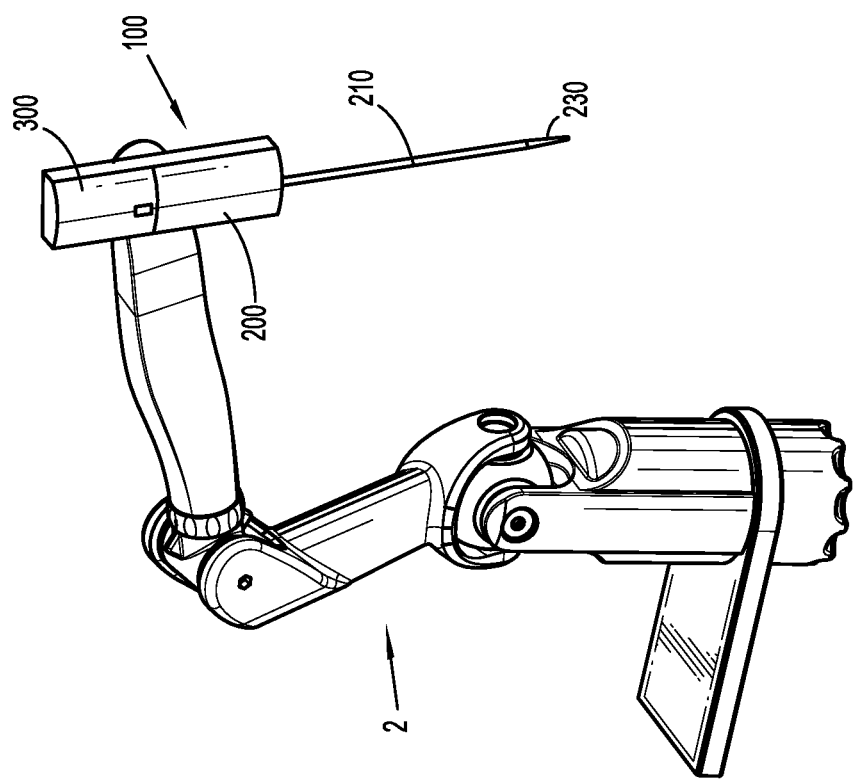
FIG. 2 is a perspective view of a robotic arm having a surgical assembly mounted thereon.
Figure 4:
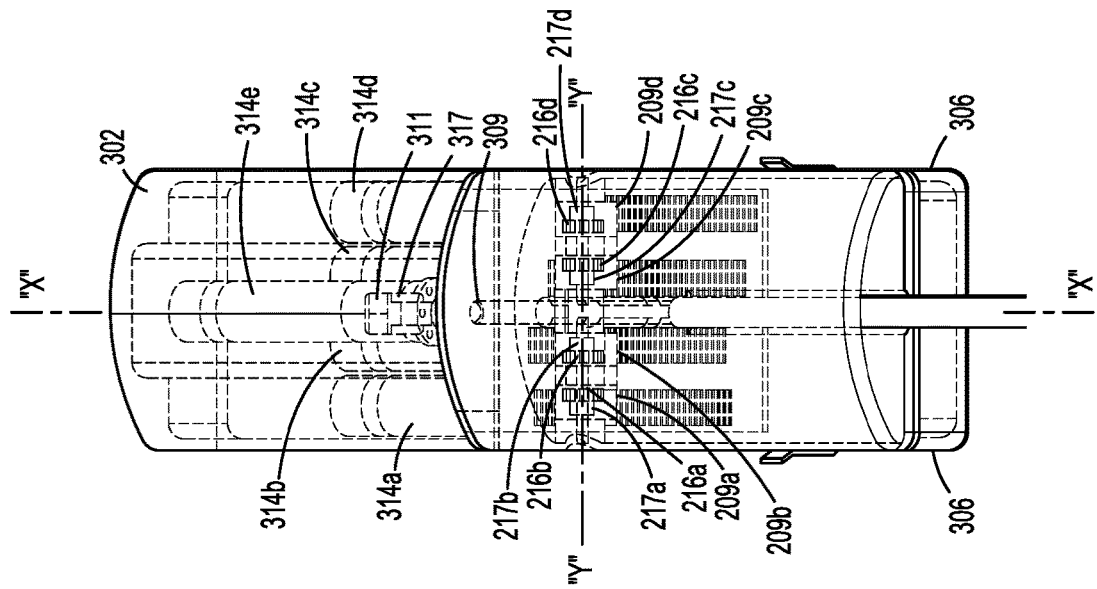
FIG. 4 is a perspective view of the surgical assembly of FIG. 2 showing portions of an instrument drive unit and the adapter portion of the surgical instrument in phantom.
Figure 3:
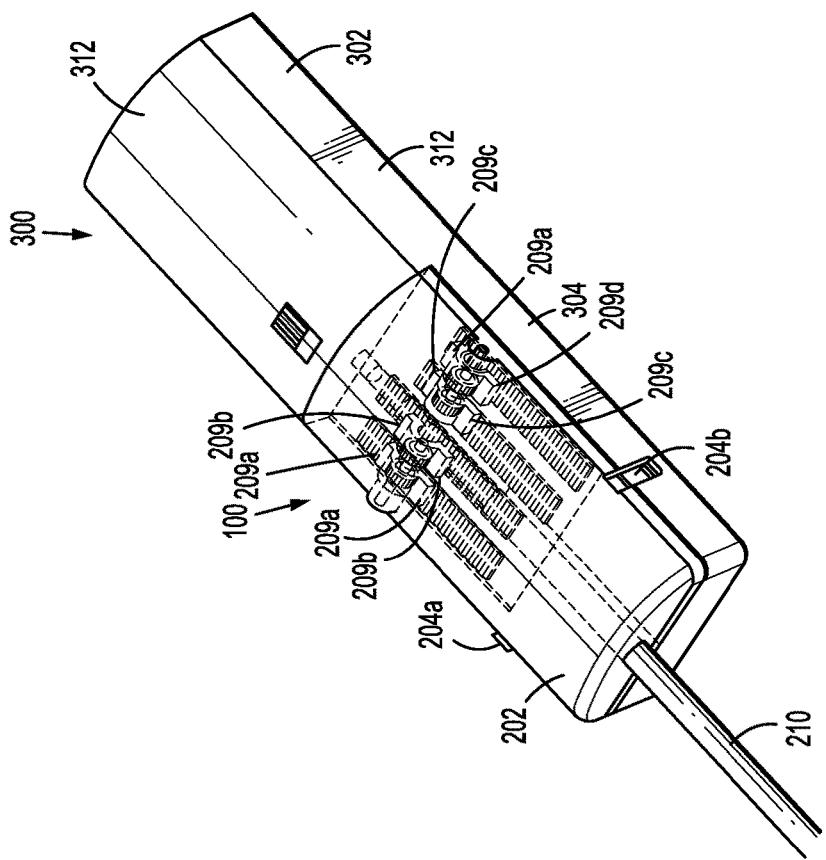
FIG. 3 is a partial, perspective view of the surgical assembly of FIG. 2 showing an adapter portion of a surgical instrument in phantom.

Turning now to FIGS. 2-4, surgical assembly 100 includes instrument drive unit 300 coupled to robotic arm 2, and a surgical instrument 200 releasably coupled to instrument drive unit 300. Instrument drive unit 300 includes a body 312 having a first housing portion 302 and a second housing portion 304 that extends distally from first housing portion 302. In particular, second housing portion 304 defines a cutout 319 (FIG. 6) configured to receive an adapter portion 202 (FIG. 3) of surgical instrument 200. Second housing portion 304 includes lateral sides 306 (FIG. 4). Each lateral side 306 defines a groove 306a, 306b (FIG. 5) configured to receive a respective tab 204a, 204b (FIG. 3) of adapter portion 202. Tabs 204a, 204b may engage respective groove 306a, 306b through, e.g., snap fit or friction fit configuration, to detachably couple surgical instrument 200 to instrument drive unit 300. In this manner, various surgical instruments may be interchangeably used with instrument drive unit 300. Body 312 of instrument drive unit 300 includes connection surfaces 308a, 308b (FIG. 5) that are configured to engage engaging surfaces 206a, 206b (FIG. 6) of adapter portion 202 of surgical instrument 200. Connection surface 308a (FIG. 5) defines a plurality of slots 310a-d (FIG. 8), and connection surface 308b defines a bore 309 (FIG. 4) as will be described below.

Figure 5:
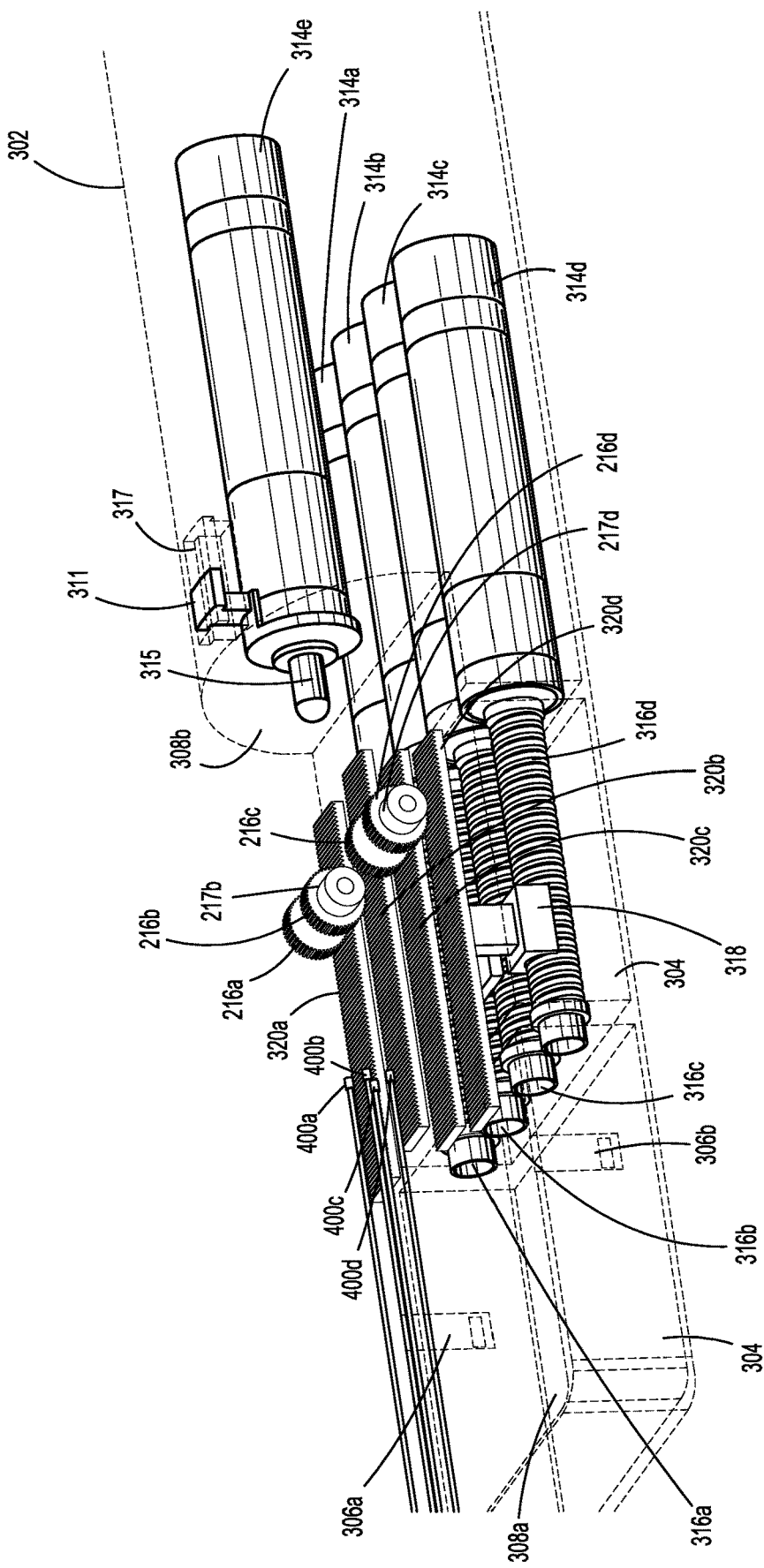
FIG. 5 is a perspective view of the instrument drive unit of FIG. 4 showing actuators and lead screws in phantom.

With reference now to FIGS. 4 and 5, instrument drive unit 300 supports a plurality of actuators or motors 314a-e and a plurality of lead screws 316a-d (FIG. 5) operatively coupled with respective motors 314a-d. Specifically, motor 314e is slidably disposed in first housing portion 302 and is coupled to a rotatable adapter 315 configured to operatively engage elongate member 210 of surgical instrument 200.

Connection surface 308b of first housing portion 302 of instrument drive unit 300 defines bore 309 (FIG. 4) configured to receive rotatable adapter 315 therethrough. First housing portion 302 further defines a slot 317 (FIG. 5) configured to slidably receive a lever 311. Lever 311 is configured to slide motor 314e along a longitudinal axis "X-X" (FIG. 4) between an extended position (FIG. 5) in which rotatable adapter 315 (FIG. 5) extends through bore 309 of connection surface 308b and a retracted position (FIG. 4) in which rotatable adapter 315 (FIG. 5) is disposed proximal of bore 309. Lever 311 may be placed in the retracted position (FIG. 4) to facilitate, e.g., attachment and detachment, of surgical instrument 200 to and from instrument drive unit 300.

With continued reference to FIG. 5, motors 314a-d are coupled with respective lead screws 316a-d. Each lead screw 316a-d is threadably associated with a non-rotatable support member or nut 318 (only one shown in FIG. 5). Each support member 318 is slidably received through respective slot 310a-d (FIG. 8) defined in connection surface 308a of second housing portion 304. Each support member 318 is coupled with a respective rack member 320a-d having teeth. Under such a configuration, actuation of respective motor 314a-d causes concomitant rotation of respective lead screw 316a-d. Rotation of respective lead screw 316a-d causes translation of respective support member 318 within respective slot 310a-d, which in turn, imparts translation to respective rack member 320a-d. Independent actuation of motors 314a-d enables independent translation of rack members 320a-d.

With reference now to FIGS. 5 and 6, surgical instrument 200 includes adapter portion 202, elongate member 210 extending from adapter portion 202, and end effector 230 (FIG. 2) at a distal end of elongate member 210. Adapter portion 202 includes engaging surfaces 206a, 206b (FIG. 6) configured to engage and/or oppose connection surfaces 308a, 308b (FIG. 5) of instrument drive unit 300, respectively. Adapter portion 202 supports a plurality of gears 216a-d (FIG. 6) on, e.g., a common axis "Y-Y" (FIG. 4), for independent rotation thereof. In particular, each gear 216a-d has a reel portion 217a-d (FIG. 4). Each reel portion 217a-d of gear 216a-d is coupled to a respective cable 400a-d (FIG. 5). Engaging surface 206b (FIG. 6) of adapter portion 202 defines a plurality of apertures 209a-d (FIG. 4). At least a portion of each gear 216a-d extends through respective aperture 209a-d, such that each gear 216a-d engages respective rack member 320a-d. In this manner, translation of rack member 320a-d causes rotation of respective gear 216a-d of adapter portion 202.

Each cable 400a-d has a first end that is coupled to respective reel portion 217a-d (FIG. 4) of respective gear 216a-d and a second end that is coupled to end effector 230 at a distal end of elongate member 210. Each cable 400a-d may be coupled to end effector 230 such that actuation of each cable 400a-d or combination thereof performs a function of end effector 230. Longitudinal translation of one or more of cables 400a-d imparts movement (e.g., rotation, pivoting, articulation, longitudinal/lateral translation, etc.) on end effector 230, or portions thereof. For instance, U.S. patent application Ser. No. 14/257,063, filed Apr. 21, 2014 (now U.S. Patent Publication No. 2015/0297199 (now U.S. Pat. No. 10,080,552)), and entitled "Adapter Assembly with Gimbal for Interconnecting Electromechanical Surgical devices and Surgical Loading Units, and Surgical Systems Thereof," the entire contents of which are hereby incorporated by reference, describes surgical stapling devices with end effectors that support distally advanceable sleds operatively coupled to a rotatable lead screw to fire surgical staples. Elongate member 210 is dimensioned to receive each of the plurality of cables 400a-d and to enable each of the plurality of cables 400 to linearly translate therethrough.

Figure 8:
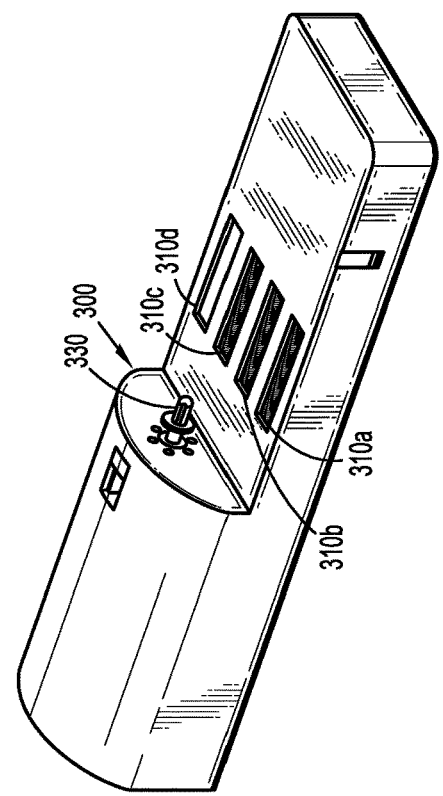
FIG. 8 is a perspective view of a body of the instrument drive unit of FIG. 7 having a plug mounted on a rotatable adapter.
Figure 7:
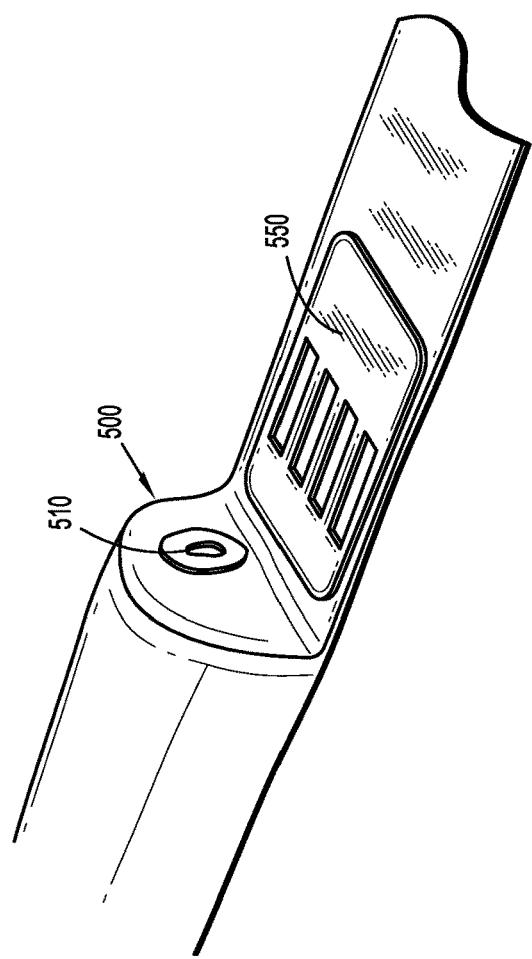
FIG. 7 is a perspective view of a drape for use with the instrument drive unit of FIG. 6.

With reference now to FIGS. 7 and 8, instrument drive unit 300 may be provided with a protective barrier or drape 500. For instance, U.S. Pat. No. 7,886,743 entitled "Sterile Drape Interface for Robotic Surgical Instrument" describes a sterile drape covering at least a portion of the robotic surgical manipulator. Instrument drive unit 300 may be covered with drape 500 prior to mounting surgical instrument 200 thereon. Drape 500 may be formed of, e.g., a flexible material. Drape 500 may include a rotation collar 510 formed of, e.g., a rigid polymer. Rotation collar 510 may be welded onto drape 500. Rotation collar 510 is configured to receive rotatable adapter 315 coupled with motor 314e. Drape 500 may further include a reinforced support 550 formed of, e.g., a rigid polymer sheet, to provide a reinforced surface on which rack members 320a-d translate. Rotatable adapter 315 may be provided with a sterile barrier plug 330 to provide a sterile barrier between the interchangeable rotating parts.

In operation, surgical instrument 200 is detachably mounted on instrument drive unit 300 supported on robotic arm 2, 3, while lever 311 of instrument drive unit 300 is in the retracted state. Gears 216a-d of adapter portion 202 engage respective rack members 320a-d. At this time, lever 311 of instrument drive unit 300 may be transitioned to the extended state such that rotatable adapter 315 coupled with motor 314e operatively engages elongate member 210 of surgical instrument 200.

With surgical instrument 200 operatively coupled to instrument drive unit 300, one or more of the plurality of motors 314a-d are activated to rotate one or more of lead screws 316a-d. Rotation of lead screw 316a-d of instrument drive unit 300 causes translation of respective rack member 320a-d, which in turn, causes rotation of respective gear 216a-d of surgical instrument 200. Rotation of respective gear 216a-d translates respective cable 400a-d. Longitudinal translation of cables 400a-d, or combination thereof, imparts movement (e.g., rotation, pivoting, articulation, longitudinal/lateral translation, etc.) on end effector 230, or portions thereof. In addition, actuation of motor 314e causes rotation of rotatable adapter 315 (about longitudinal axis "X-X") which is operatively coupled with elongate member 210 of surgical instrument 200. In this manner, actuation of motor 314e causes rotation of elongate member 210 of surgical instrument 200.

Persons skilled in the art will understand that the structures and methods specifically described herein and shown in the accompanying figures are non-limiting exemplary embodiments, and that the description, disclosure, and figures should be construed merely as exemplary of particular embodiments. It is to be understood, therefore, that the present disclosure is not limited to the precise embodiments described, and that various other changes and modifications may be effected by one skilled in the art without departing from the scope or spirit of the disclosure. Additionally, the elements and features shown or described in connection with certain embodiments may be combined with the elements and features of certain other embodiments without departing from the scope of the present disclosure, and that such modifications and variations are also included within the scope of the present disclosure. Accordingly, the subject matter of the present disclosure is not limited by what has been particularly shown and described.

The invention claimed is:

1. A surgical system for selective connection to a robotic arm comprising:
   an instrument drive unit including a plurality of actuators and a plurality of translatable members, each translatable member of the plurality of translatable members operatively coupled with a respective one of the plurality of actuators; and
   a surgical instrument detachably associated with the instrument drive unit, the surgical instrument including:
      an adapter portion having a plurality of rotatable members operatively associated with the plurality of translatable members of the instrument drive unit, each rotatable member of the plurality of rotatable members independently rotatable about a common axis in response to actuation of the respective one of the plurality of translatable members; and
      an end effector operatively coupled with the plurality of rotatable members of the adapter portion.

2. The surgical system according to claim 1, wherein rotation of a first actuator of the plurality of actuators of the instrument drive unit imparts rotation to a first rotatable member of the plurality of rotatable members of the adapter portion.

3. The surgical system according to claim 2, wherein rotation of the first actuator causes translation of a first translatable member of the plurality of translatable members, which in turn, causes rotation of the first rotatable member of the adapter portion.

4. The surgical system according to claim 3, wherein the first rotatable member includes a gear portion having teeth configured to mesh with teeth of the first translatable member of the instrument drive unit.

5. The surgical system according to claim 1, wherein a second actuator of the plurality of actuators of the instrument drive unit is movable between a retracted position in which the second actuator is operatively disengaged from the end effector and an extended position in which the second actuator is operatively engaged with the end effector.

6. The surgical system according to claim 1, wherein the end effector further includes an elongate member interconnecting the adapter portion and the end effector.

7. The surgical system according to claim 1, wherein the surgical instrument further includes a plurality of cables, each cable operatively coupling a respective one of the plurality of rotatable members to the end effector.

8. The surgical system according to claim 7, wherein a first rotatable member of the plurality of rotatable members includes a first reel configured to wind a first cable of the plurality of cables thereabout upon rotation of the first rotatable member.

9. The surgical system according to claim 1, wherein the plurality of translatable members of the instrument drive unit is coplanar.

10. The surgical system according to claim 1, wherein the common axis defined by the plurality of rotatable members of the adapter portion is in superposed relation with a plane defined by the plurality of translatable members of the instrument drive unit.

11. The surgical system according to claim 2, wherein the end effector is operatively coupled with the first rotatable member such that rotation of the first rotatable member effects a first function of the end effector.

12. The surgical system according to claim 11, wherein the end effector is operatively coupled with a third rotatable members of the plurality of the rotatable members such that rotation of the third rotatable member effects a second function of the end effector.

13. A robotic surgical assembly comprising:
    a robotic arm;
    an instrument drive unit secured to the robotic arm, the instrument drive unit including first and second actuators and first and second translatable members operatively coupled with the respective first and second actuators, the first and second translatable members defining a first common plane; and
    a surgical instrument detachably coupled to the instrument drive unit, the surgical instrument including an adapter portion having first and second rotatable members operatively associated with the first and second translatable members, the first and second rotatable members being operatively independent of each other and rotatable about a common axis, the first and second rotatable members being rotatable in response to actuation of the respective first and second actuators.

14. The robotic surgical assembly according to claim 13, wherein actuation of the first actuator causes translation of the first translatable member, which in turn, causes rotation of the first rotatable member of the adapter portion of the surgical instrument.

15. The robotic surgical assembly according to claim 14, wherein the surgical instrument further includes a first cable having a first end coupled to the first rotatable member and a second end operatively associated with an end effector of the surgical instrument.

16. The robotic surgical assembly according to claim 15, wherein rotation of one of the first and second rotatable members causes a first function of the end effector of the surgical instrument.

17. The robotic surgical assembly according to claim 16, wherein the surgical instrument further includes a second cable having a third end coupled to the second rotatable member and a fourth end operatively associated with the end effector, wherein rotation of the first and second rotatable members effects a second function of the end effector.

18. The robotic surgical assembly according to claim 15, wherein the first rotatable member includes a reel portion configured to wind the first cable thereabout upon rotation of the first rotatable member.

19. The robotic surgical assembly according to claim 14, wherein the common axis is in registration with the first common plane.

20. The robotic surgical assembly according to claim 14, wherein the plurality of actuators are on a second common plane.

* * * * *